United States Patent
De Angelis et al.

(10) Patent No.: US 7,906,683 B2
(45) Date of Patent: Mar. 15, 2011

(54) PROCESS FOR THE REMOVAL BY OXIDATION, OF MERCAPTANS CONTAINED IN HYDROCARBONS

(75) Inventors: Alberto De Angelis, Legnano (IT); Paolo Pollesel, San Donato Milanese (IT)

(73) Assignee: ENI S.p.A., Rome (IT)

( * ) Notice: Subject to any disclaimer, the term of this patent is extended or adjusted under 35 U.S.C. 154(b) by 796 days.

(21) Appl. No.: 11/816,755

(22) PCT Filed: Feb. 15, 2006

(86) PCT No.: PCT/EP2006/001443
§ 371 (c)(1),
(2), (4) Date: Oct. 1, 2007

(87) PCT Pub. No.: WO2006/094612
PCT Pub. Date: Sep. 14, 2006

(65) Prior Publication Data
US 2008/0207951 A1    Aug. 28, 2008

(30) Foreign Application Priority Data
Mar. 3, 2005   (IT) .............................. MI2005A0322

(51) Int. Cl.
*C07C 321/00*   (2006.01)

(52) U.S. Cl. .......................................... 568/26
(58) Field of Classification Search ................. None
See application file for complete search history.

(56) References Cited

U.S. PATENT DOCUMENTS

| 4,374,042 | A | * | 2/1983 | Frame ............................ 502/29 |
| 4,490,246 | A | * | 12/1984 | Verachtert ..................... 208/206 |
| 5,422,086 | A | * | 6/1995 | Bowman ........................ 423/220 |
| 5,621,097 | A | * | 4/1997 | Brown et al. .................. 540/342 |
| 6,294,699 | B1 | * | 9/2001 | Refvik et al. ................... 568/26 |
| 7,179,366 | B2 | * | 2/2007 | Harle et al. ................... 208/123 |
| 7,553,473 | B2 | * | 6/2009 | De Angelis et al. ....... 423/573.1 |
| 7,608,231 | B2 | * | 10/2009 | Bellussi et al. .............. 423/224 |
| 2007/0178033 | A1 | | 8/2007 | De Angelis et al. |

FOREIGN PATENT DOCUMENTS

| WO | 2004 014832 | 2/2004 |
| WO | 2005 075351 | 8/2005 |

* cited by examiner

*Primary Examiner* — Daniel M Sullivan
*Assistant Examiner* — Chukwuma O Nwaonicha
(74) *Attorney, Agent, or Firm* — Oblon, Spivak, McClelland, Maier & Neustadt, L.L.P.

(57) ABSTRACT

The mercaptans R—SH contained in a hydrocarbon stream are oxidized to the corresponding (di)sulfides by means of a redox system which comprises trivalent iron and a heteropolyacid which allows the complete reoxidation of the reduced iron also with air.

12 Claims, No Drawings

PROCESS FOR THE REMOVAL BY OXIDATION, OF MERCAPTANS CONTAINED IN HYDROCARBONS

The present invention relates to a process for the removal, by oxidation, of mercaptans contained in hydrocarbons.

More specifically, the present invention relates to a process for the oxidation of mercaptans contained in hydrocarbon fractions or in natural or associated gas (coming from an oil field).

Even more specifically, the present invention relates to a process for the removal of mercaptans contained in natural or associated gas (hereinafter both defined as natural gas).

Mercaptans are organic compounds containing sulfur, which are often present in natural gas, in associated gas and in liquid hydrocarbon fractions such as fuels, kerosene, diesel fuel, etc. Mercaptans are characterized by the presence of sulfur as an —SH group and described by the general formula R—SH wherein R can be either an aliphatic group or an aromatic group. Mercaptans must be removed or converted into other compounds as they have an unpleasant odour, are toxic and can cause significant problems of corrosion.

There are substantially two kinds of processes for eliminating mercaptans: processes in which the mercaptans are converted into the corresponding disulfides (extraction and sweetening processes) and processes in which the mercaptans are eliminated by irreversible reactions with generally inorganic compounds (scrubbing methods).

The first types of processes are used for eliminating considerable quantities of mercaptans from hydrocarbons from 200 kg a day of equivalent sulfur up to 30 tons and more. Scrubbing methods, on the other hand, are applied to eliminate, from gaseous or liquid streams, mercaptans, if present, in quantities lower than 200 Kg of equivalent sulfur.

Extraction and sweetening processes are more important from the point of view of economical impact, and are therefore those in which it is of greater interest to improve the characteristics of the system.

The extraction processes, in which the lighter mercaptans are extracted from a gaseous stream and separated by converting them into disulfides, and sweetening processes, in which the mercaptans are oxidized to disulfides (which remain in the sweetened liquid), are carried out in strongly alkaline means. For an effecting running of the process, in fact, caustic soda is used in concentrations ranging from 10 to 14% and a pre-washing with soda is also effected for the removal of hydrogen sulfide and other acid compounds possibly presents in the fluid to be treated.

The main critical aspect of this type of process therefore consists in the fact that at the end of the treatment for the removal of mercaptans, large quantities of caustic soda are present, contaminated by sulfurated compounds, whose disposal represents a problem from both an economical and ecological point of view.

It would consequently be extremely useful to be able to avail of a process which does not require a pre-washing with strongly alkaline solutions, using an acid solution which can be easily recycled at the end of each catalytic cycle.

The Applicants have now found, and this forms an object of the present invention, better defined in the enclosed claims, that it is possible to advantageously effect the oxidation reaction of mercaptans, to the corresponding disulfides, in an acid environment, with a solution of trivalent iron and in the presence of a modest quantity of a heteropolyacid having redox properties. In this way, iron is capable of effectively oxidizing the mercaptan to sulfide and can be easily reoxidized by the oxygen of air, due to the presence of the heteropolyacid.

The aqueous iron solution and the heteropolyacid can be conveniently recycled and used for different subsequent reaction/regeneration cycles.

The system described above can be dissolved in an aqueous solution and is preferably applied to the removal of mercaptans from gaseous streams such as, for example, natural gas or the like, or be supported on suitable carriers, such as activated carbons, for example, and be used for the removal of mercaptans from liquid hydrocarbon fractions.

Carrying out the reaction with acid pH, in the presence of heteropolyacid has numerous advantages and more specifically:

a) a pre-washing of the stream to be treated is not required, thus avoiding the consumption of chemicals (NaOH) due to the reaction of acid compounds present with soda, such as hydrogen sulfide, carbon dioxide (in gaseous streams) or naphthene acids in the case of liquid fractions;

b) as the reaction is not carried out in an alkaline environment, it does not consume caustic products (by carbonation);

c) there is not the problem of disposing of alkaline solutions contaminated by sulfur based products, which has strong implications from both an environmental and economical point of view.

The heteropolyacids which are active in promoting the oxidation of reduced iron are mainly hetero-polyacids having redox properties such as, for example, those described by general formula (I):

$$H_nXV_yM_{(12-y)}O_{40} \quad (I)$$

wherein n is an integer ranging from 3 to 6 and is equal to 3+y, X is an element selected from P, Si, As, B, Ge, y is an integer ranging from 1 to 3 and M consists of Mo or W.

The presence of the hetero-polyacid in solution allows an easy, complete and rapid re-oxidization of the reduced solution of iron salts, which in the absence of the heteropolyacid are only partially re-oxidized by the air or oxygen and with extremely slow kinetics.

In a particular application, the heteropolyacid is used in solid form.

Possible examples of solid forms insoluble in water are:

1) partial or complete salification with metals whose salts are insoluble such as, for example, cesium, potassium, or with ammonium prepared according to the method described in literature by A. Corma et al. in J. of Catal., 1996, vol. 164, 422-432; silver, prepared according to the method described in literature by J. B. Moffat et al. in Cat. Lett., 1998, vol. 55, 183-188; thallium (I), prepared according to the method described in literature by J. B. Moffat et al. in J. of Catal., 1998, vol. 177, 335-342;

2) supporting and immobilization on silica in accordance with the literature, for example Y. Izumi et al., Appl. Catal. A, 1999, vol. 181, 277-282;

3) supporting and immobilization on mesoporous molecular sieves, such as HMS and MCM-41, according to what is described in literature, for example, by W. Chu et al. in Cat. Lett., 1996, vol. 42, 201-208;

4) supporting and immobilization on activated carbon according to what is described in literature for example by M. E. Chimienti et al. in Appl. Catal. A, 2001, vol. 208, 7-19.

In the solid and insoluble-in-water form, the heteropolyacid can be used in a slurry reactor, where the solid is dispersed in the process liquid, or in a fixed bed reactor. In both applications, the catalyst is suitably formed for example into microspheres, for the slurry reactor, or into pellets, for the fixed bed reactor, according to the known technologies.

In the case of use in the solid, insoluble-in-water form, the hetero-polyacid remains confined in the oxidation reactor alone.

It has been surprisingly found that the oxidation reaction of mercaptans to disulfides in the presence of heteropolyacids can be advantageously carried out without the solution of trivalent iron, when the hetero-polyacids itself contains instead of the hetero-element X, a metal capable of exerting redox properties such as, for example, a generic hetero-polyacids having formula (II):

$$H_nMeM_{12}O_{40} \quad (II)$$

wherein n is an integer ranging from 2 to 7, Me can be Fe, Co, Mn, Cu, whereas M consists of Mo or W.

In this case, it is the metal Me, in the centre of the heteropolyacid structure, which oxidizes the mercaptan to disulfide and is reduced to a lower oxidation state than the initial one. The metal Me is then reoxidized to the initial oxidation state by simply bubbling air into the reaction solution, after filtering the sulfur produced.

Some illustrative and non-limiting examples are provided for a better understanding of the present invention and for its embodiment.

EXAMPLE 1

Synthesis of the Acid $H_4PVMo_{11}O_{40}$ 1.22 g of sodium metavanadate (equal to 0.01 moles) are dissolved in 100 ml of distilled water and 3.58 g of $Na_2HPO.12H_2O$ (equal to 0.01 moles) and finally 26.61 g of $Na_2MoO_4.2H_2O$ (equal to 0.11 moles) are subsequently added. 20 g of nitric acid at 60% are finally added to this solution obtaining the condensation of the heteropolyacid which is revealed by the formation of a dark red colouring. The solution is brought to a small volume until it starts crystallizing, sulfuric acid 2N and ethyl ether are then added in an equal volume applying the Drechsel method (see Handbook of preparative inorganic chemistry by G. Brauer Academic press—New York 1965), extracting the heteropolyacid as a complex with ethyl ether.

Upon evaporating the ether, the heteropolyacid $H_4PVMo_{11}O_{40}$ is obtained in the form of orange crystals. The X-ray spectrum of this compound perfectly corresponds to that specified in literature (O. Akba et al. Synth. React. Inorg. Met-org. Chem., 27(9), 1399-1415 (1997)).

EXAMPLE 2

Synthesis of the Acid $H_5PV_2Mo_{10}O_{40}$ 7.32 g of sodium metavanadate (equal to 0.06 moles) are dissolved in 100 ml of distilled water and 3.58 g of $Na_2HPO.12H_2O$ (equal to 0.01 moles) and finally 24.19 g of $Na_2MoO_4.2H_2O$ (equal to 0.1 mole) are subsequently added. 20 g of nitric acid at 60% are finally added to this solution obtaining the condensation of the heteropolyacid which is revealed by the formation of a dark red colouring. The solution is brought to a small volume until it starts crystallizing, sulfuric acid 2N and ethyl ether are then added in an equal volume applying the Drechsel method (see Handbook of preparative inorganic chemistry by G. Brauer Academic press—New York 1965), extracting the hetero-polyacid as a complex with ethyl ether.

Upon evaporating the ether, the heteropolyacid $H_5PV_2Mo_{10}O_{40}$ is obtained in the form of orange crystals. The X-ray spectrum of this compound perfectly corresponds to that specified in literature (O. Akba et al. Synth. React. Inorg. Met-org. Chem., 27(9), 1399-1415 (1997)).

EXAMPLE 3

Synthesis of the Acid $H_6PV_3Mo_9O_{40}$ 14.64 g of sodium metavanadate (equal to 0.12 moles) are dissolved in 200 ml of distilled water and 7.16 g of $Na_2HPO.12H_2O$ (equal to 0.02 moles) and finally 21.76 g of $Na_2MoO_4.2H_2O$ (equal to 0.09 moles) are subsequently added. 40 g of nitric acid at 60% are finally added to this solution obtaining the condensation of the heteropolyacid which is revealed by the formation of a dark red colouring. The solution is brought to a small volume until it starts crystallizing, sulfuric acid 2N and ethyl ether are then added in an equal volume applying the Drechsel method (see Handbook of preparative inorganic chemistry by G. Brauer Academic press—New York 1965), extracting the hetero-polyacid as a complex with ethyl ether.

Upon evaporating the ether, the hetero-polyacid $H_6PV_3Mo_9O_{40}$ is obtained in the form of dark red crystals. The X-ray spectrum of this compound perfectly corresponds to that specified in literature (O. Akba et al. Synth. React. Inorg. Met-org. Chem., 27(9), 1399-1415 (1997)).

EXAMPLE 4

Synthesis of the Acid $H_6PV_3W_9O_{40}$ 14.64 g of sodium metavanadate (equal to 0.12 moles) are dissolved in 200 ml of distilled water and 7.16 g of $Na_2HPO.12H_2O$ (equal to 0.02 moles) and finally 29.70 g of $Na_2WO_4.2H_2O$ (equal to 0.09 moles) are subsequently added. 40 g of nitric acid at 60% are finally added to this solution obtaining the condensation of the heteropolyacid which is revealed by the formation of a dark red colouring. The solution is brought to a small volume until it starts crystallizing, sulfuric acid 2N and ethyl ether are then added in an equal volume applying the Drechsel method (see Handbook of preparative inorganic chemistry by G. Brauer Academic press—New York 1965), extracting the hetero-polyacid as a complex with ethyl ether.

Upon evaporating the ether, the heteropolyacid $H_6PV_3W_9O_{40}$ is obtained in the form of dark red crystals. The X-ray spectrum of this compound perfectly corresponds to that specified in literature (O. Akba et al. Synth. React. Inorg. Met-org. Chem., 27(9), 1399-1415 (1997)).

EXAMPLE 5

Synthesis of the Heteropolyacid-Based Catalyst Supported on Activated Carbon

A sample of activated carbon equal to 20 g is first washed with HCl 0.1 N, then with NaOH 0.1 N and finally with distilled water until neutrality of the water. The sample of activated carbon is then suspended in a solution of nitric acid at 10% by weight and is then refluxed for three hours in order to eliminate the oxidizable species present on the surface of the carbon. The sample is then washed with distilled water until neutrality and dried at 150° C. for 12 hours.

10 g of the sample of activated carbon thus obtained are treated with 100 ml of absolute ethyl alcohol in which 10 g of $Fe(NO_3)_3.9H_2O$ and 10 g of $H_6PV_3W_9O_{40}$ are dissolved. The suspension is stirred for 3 hours at room temperature, filtered on a porous glass septum and washed with anhydrous ethyl alcohol. The catalyst thus obtained is dried at 150° C. for 12 hours.

EXAMPLE 6

Oxidation of t-butylmercaptan with a Solution of Trivalent iron and $H_6PV_3W_9O_{40}$ The tests were carried out by dissolving 5.42 g of Fe $(NO_3)_3 \cdot 9H_2O$ (0.0134 moles) and 5.42 g of $H_6PV_3W_9O_{40}$ (0.00195 moles) in 500 ml of distilled water, with a molar ratio Fe/HPA equal to 6.9/1. 1.21 g of t-butylmercaptan (0.0134 moles) are added to this orange-coloured limpid solution, thus simulating the flow of a gaseous stream containing mercaptans in the aqueous solution of hetero-polyacid and ferric salt. This mercaptan is selected as it is particularly difficult to oxidize to the corresponding disulfide. The reactor is closed and brought to a temperature of 40° C.

The mixture is stirred for six hours, cooled to 10° C., to avoid the possible loss of mercaptan (boiling point of 62° C.), and 50 ml of toluene are then added. The mixture is poured into a separating funnel and the organic phase is extracted, which is analyzed by means of gas chromatography.

A conversion of t-butylmercaptan of 80% is obtained, with a selectivity of 53% to diterbutyldisulfide and 47% to diterbutylsulfide, respectively.

EXAMPLE 7

Oxidation of t-butylmercaptan with a Solution of Trivalent Iron and $H_6PV_3Mo_9O_{40}$ The tests were carried out by dissolving 5.42 g of Fe $(NO_3)_3 \cdot 9H_2O$ (0.0134 moles) and 5.42 g of $H_6PV_3Mo_9O_{40}$ (0.0032 moles) in 500 ml of distilled water, with a molar ratio Fe/HPA equal to 4.2/1. 1.21 g of t-butylmercaptan (0.0134 moles) are added to this orange-coloured limpid solution, thus simulating the flow of a gaseous stream containing mercaptans in the aqueous solution of heteropolyacid and ferric salt. This mercaptan is selected as it is particularly difficult to oxidize to the corresponding disulfide. The reactor is closed and brought to a temperature of 40° C.

The mixture is stirred for six hours, cooled to 10° C., to avoid the possible loss of mercaptan (boiling point of 62° C.), and 50 ml of toluene are then added. The mixture is poured into a separating funnel and the organic phase is extracted, which is analyzed by means of gas chromatography.

A conversion of t-butylmercaptan of 70% is obtained, with a selectivity of 58% to diterbutyldisulfide and 42% to diterbutylsulfide, respectively.

EXAMPLE 8

Oxidation of t-butylmercaptan with a Solution of Trivalent Iron and $H_6PV_3Mo_9O_{40}$ The tests were carried out by dissolving 10.84 g of $Fe(NO_3)_3 \cdot 9H_2O$ (0.0268 moles) and 9.5 g of $H_6PV_3Mo_9O_{40}$ (0.00383 moles) in 500 ml of distilled water, with a molar ratio Fe/HPA equal to 7/1. 1.21 g of t-butylmercaptan (0.0134 moles) are added to this orange-coloured limpid solution, thus simulating the flow of a gaseous stream containing mercaptans in the aqueous solution of heteropolyacid and ferric salt. This mercaptan is selected as it is particularly difficult to oxidize to the corresponding disulfide. The reactor is closed and brought to a temperature of 40° C.

The mixture is stirred for six hours, cooled to 10° C., to avoid the possible loss of mercaptan (boiling point of 62° C.), and 50 ml of toluene are then added. The mixture is poured into a separating funnel and the organic phase is extracted, which is analyzed by means of gas chromatography.

A conversion of t-butylmercaptan of 86% is obtained, with a selectivity of 45% to diterbutyldisulfide and 55% to diterbutylsulfide, respectively.

EXAMPLE 9

Regeneration of the Reduced Iron Solution Containing Hetero-polyacid

The reduced iron solution, coming from the previous reaction (example 8) is reoxidized by treating it with an air flow at 80° C., for two hours. The content of trivalent iron is titrated, according to one of the methods described in literature (for example according to what is described by A. Hulanicki in Talanta, volume 18, 239-245, 1971) and the complete reoxidation of the solution is measured. An analogous solution prepared without the heteropolyacid does not lead to complete reoxidation, not even after 48 hours of treatment at 80° C. in an air flow. Not only, but the reduced solution not containing the heteropolyacid upon prolonged heating decomposes with a considerable development of nitrous vapours and the formation of a precipitate of iron hydroxide.

EXAMPLE 10

Oxidation of t-butylmercaptan with a Solution of Trivalent Iron and $H_6PV_3Mo_9O_{40}$ Regenerated According to the Previous Example 1.21 g of t-butylmercaptan (0.0134 moles) are added to the solution of iron and hetero-polyacid regenerated according to what is described in the previous example 9, thus simulating the flow of a gaseous stream. The reactor is closed and brought to a temperature of 40° C.

The mixture is stirred for six hours, cooled to 10° C., to avoid the possible loss of mercaptan (boiling point 62° C.), and 50 ml of toluene are then added. The mixture is poured into a separating funnel and the organic phase is extracted, which is analyzed by means of gas chromatography.

A conversion of t-butylmercaptan of 87% is obtained, with a selectivity of 47% to diterbutyldisulfide and 53% to diterbutylsulfide, respectively.

The invention claimed is:

1. A process for the removal, by oxidation, of mercaptans contained in hydrocarbons, which comprises:
   a) putting a hydrocarbon, or a mixture of hydrocarbons, containing one or more mercaptans having the general formula R—SH, wherein R represents a $C_1$-$C_{50}$ aliphatic or $C_6$-$C_{30}$ aromatic hydrocarbon, in contact with a system comprising trivalent iron, a heteropolyacid having redox properties, as such or partially salified with an alkaline metal or with ammonium, and optionally water, said hetero-polyacid being selected from those having general formula (I):

$$H_n X V_y M_{(12-y)} O_{40} \qquad (I)$$

wherein n is an integer ranging from 3 to 6 and is equal to 3+y; X is an element selected from P, Si, As, B, and Ge; y is an integer ranging from 1 to 3; and M consists of Mo or W;

b) oxidizing the mercaptans to the corresponding (di)sulfides by the oxidizing effect of the trivalent iron which is reduced to bivalent iron;

c) separating the optional aqueous phase from the organic phase;

d) reoxidizing the bivalent iron to trivalent iron with a gaseous stream containing oxygen; and e) recycling the system comprising trivalent iron, heteropolyacid and optionally water to the oxidation step (a).

2. The process according to claim 1, wherein the heteropolyacid is used in a solid form, insoluble in water, selected from:

compounds which are partially or completely salified with metals, whose salts are insoluble, selected from cesium, potassium, silver and thallium(I) or with ammonium;

compounds which are supported and immobilized on silica;

compounds which are supported and immobilized on mesoporous molecular sieves; and compounds which are supported and immobilized on activated carbon.

3. The process according to claim 1, wherein the trivalent iron is present as a salt of an inorganic acid.

4. The process according to claim 3, wherein the acid is nitric acid.

5. The process according to claim 1, wherein the trivalent iron is present in the solution in concentrations ranging from 0.01 to 10 moles/l.

6. The process according to claim 1, wherein said heteropolyacid compound (I) is present in concentrations ranging from 0.01 to 0.3 moles/l.

7. The process according to claim 5, wherein the molar ratio of the heteropolyacid compound (I)/trivalent iron ranges from 1/1 to 1/30.

8. The process according to claim 1, wherein the oxidation reaction takes place in the presence of water with a pH ranging from 0 to 6.

9. The process according o claim 1, wherein the hydrocarbon is natural gas.

10. The process according to claim 1, wherein the mercaptans are present in the hydrocarbon fed at a concentration ranging from 100 ppm to 5% by weight.

11. The process according to claim 1, wherein the reoxidation step takes place at a temperature ranging from 20 to 100° C. and at atmospheric pressure or at a pressure ranging from atmospheric pressure to 15 atm.

12. The process according to claim 1, wherein the gaseous stream containing oxygen consists of air, air enriched in oxygen, and oxygen.

* * * * *